United States Patent [19]

Nakakoshi et al.

[11] Patent Number: 5,098,535

[45] Date of Patent: Mar. 24, 1992

[54] PROCESS FOR PREPARING 14-α-HYDROXY-4-ANDROSTENE-3,6,17-TRIONE

[75] Inventors: Masamichi Nakakoshi, Utsunomiya; Kohji Tamura, Yono; Makoto Yoshihama; Nobuo Miyata, both of Utsunomiya, all of Japan

[73] Assignee: Snow Brand Milk Products Co., Ltd., Hokkaido, Japan

[21] Appl. No.: 475,502

[22] Filed: Feb. 6, 1990

[30] Foreign Application Priority Data

Feb. 7, 1989 [JP] Japan .................................. 1-027824

[51] Int. Cl.$^5$ .............................................. C07C 45/00
[52] U.S. Cl. ........................... 204/157.91; 204/157.93; 204/157.94; 552/615
[58] Field of Search .................. 552/615; 204/157.78, 204/157.93, 157.94, 157.99, 157.9, 157.91

[56] References Cited

FOREIGN PATENT DOCUMENTS 63-192794 8/1988 Japan .

*Primary Examiner*—John F. Niebling
*Assistant Examiner*—Isabelle R. McAndrews
*Attorney, Agent, or Firm*—Millen, White & Zelano

[57] ABSTRACT

A process for the preparation in high yield of 14α-hydroxy-4-androstene-3,6,17-trione which has an aromatase inhibition activity and is useful as an antitumor agent, in which the 6β-hydroxyl group of 6β, 14α-dihydroxy-4-androstene-3,17-dione is selectively oxidized with the aid of visible light energy.

6 Claims, 5 Drawing Sheets

PROCESS FOR PREPARING 14-α-HYDROXY-4-ANDROSTENE-3,6,17-TRIONE

BACKGROUND OF THE INVENTION

1. Field of the Invention

The present invention relates to a process for preparing 14α-hydroxy-4-androstene-3,6,17-trione, and particularly to a process for preparing said compound easily and in high yield by oxidation caused by light.

2. Description of the Prior Art

Steroids show various physiological activities due to their tertial configurations. In particular, it is now evident that such physiological activities are greatly affected by whether oxygen atoms bound to the steroid skeleton are those of hydroxyl groups or those of double-bonded oxygens. Consequently, various methods for the oxidation of the hydroxyl groups bound to the steroid backbones and for reduction of carbonyl groups thereof have been investigated.

The present inventors previously found that 6β,14α-dihydroxy-4-androstene-3,17-dione was produced by microbial transformation of steroid when 4-androstene-3,17-dione was added as a substrate to a culture medium for *Acremonium strictum*, and thus applied for a patent as Japanese Patent Application No. 24598/1987 since the compound has a strong aromatase inhibitory activity. Thereafter, as a result of intensive study on 6β,14α-dihydroxy-4-androstene-3,17-dione, the present inventors confirmed that 14α-hydroxy-4-androstene-3,6,17-trione has a stronger aromatase inhibitory activity than 6β,14α-dihydroxy-4-androstene-3,17-dione and that 14α-hydroxy-4-androstene-3,6,17-trione is useful as an antitumor agent, and then applied for a patent as Japanese Patent Application No. 24594/1987. These patent applications by the present inventors have been applied in an integrated form in U.S. Ser. No. 279,596 and in EP Appln. 88.901462.7.

14-α-hydroxy-4-androstene-3,6,17-trione is a compound having the following formula.

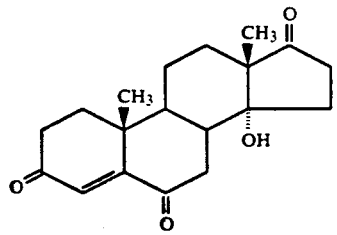

In order to obtain 14-α-hydroxy-4-androstene-3,6,17-trione, the hydroxyl group at the 6β position of 6β,14α-dihydroxy-4-androstene-3,17-dione is selectively oxidized as mentioned above using an oxidizing agent, wherein the use of activated manganese dioxide or chromic acid as the agent is required.

Steroid compounds in which an oxygen atom is bound to the carbon at position 6, not being limited to the compound above, have prominent physiological activities and hence various investigations have been conducted. However, most of the compounds have been obtained by oxidation with the use of metal catalysts or oxidizing agents such as activated manganese dioxide and chromic acid.

However, in the oxidation reaction using such oxidizing agents, in order to remove metal catalysts such as chromium or manganese and to remove excessive oxidizing agents remaining in the reaction system, complicated steps such as extraction of the solvents or fractionation using silica gel chromatography were required. Moreover, the recovery of the desired compound was not necessarily satisfactory.

Introduction of a hydroxyl group to position 6β using excitation energy with the aid of light has been reported by R. Gandi et al. (Journal of Organic Chemistry 32, 2647-2649, 1967). However, a process for oxidizing a hydroxyl group at position 6β of steroid compounds with the aid of light has not been reported and not yet known.

SUMMARY OF THE INVENTION

In the course of the intensive study on the oxidation of steroids having a 6β-hydroxyl group, the present inventors have discovered that 14α-hydroxy-4-androstene-3,6,17-trione can be obtained in a high yield by dissolving the above-mentioned 6β,14α-dihydroxy-4-androstene-3,17-dione in an organic solvent, sealing the reaction system after blowing oxygen therein and selectively oxidizing the 6β-hydroxyl group by radiating with light containing visible light.

Hence, according to the method of the present invention, it is possible to obtain 14-α-hydroxy-4-androstene-3,6,17-trione, which is useful as an antitumor agent, in a highly purified form in a simple manner and in a high yield, by selectively oxidizing the 6β-hydroxyl group of 6β,14α-dihydroxy-4-androstene-3,6,17-trione with the aid of light energy. Furthermore, the use of oxidizing agents, catalysts or the like are not required, so that production at low cost can be achieved industrially.

BRIEF DESCRIPTION OF THE DRAWINGS

The Figures attached show the characteristics of 14α-hydroxy-4-androstene-3,6,17-trione.

DETAILED DESCRIPTION AND THE PREFERRED EMBODIMENTS

Figure 1:
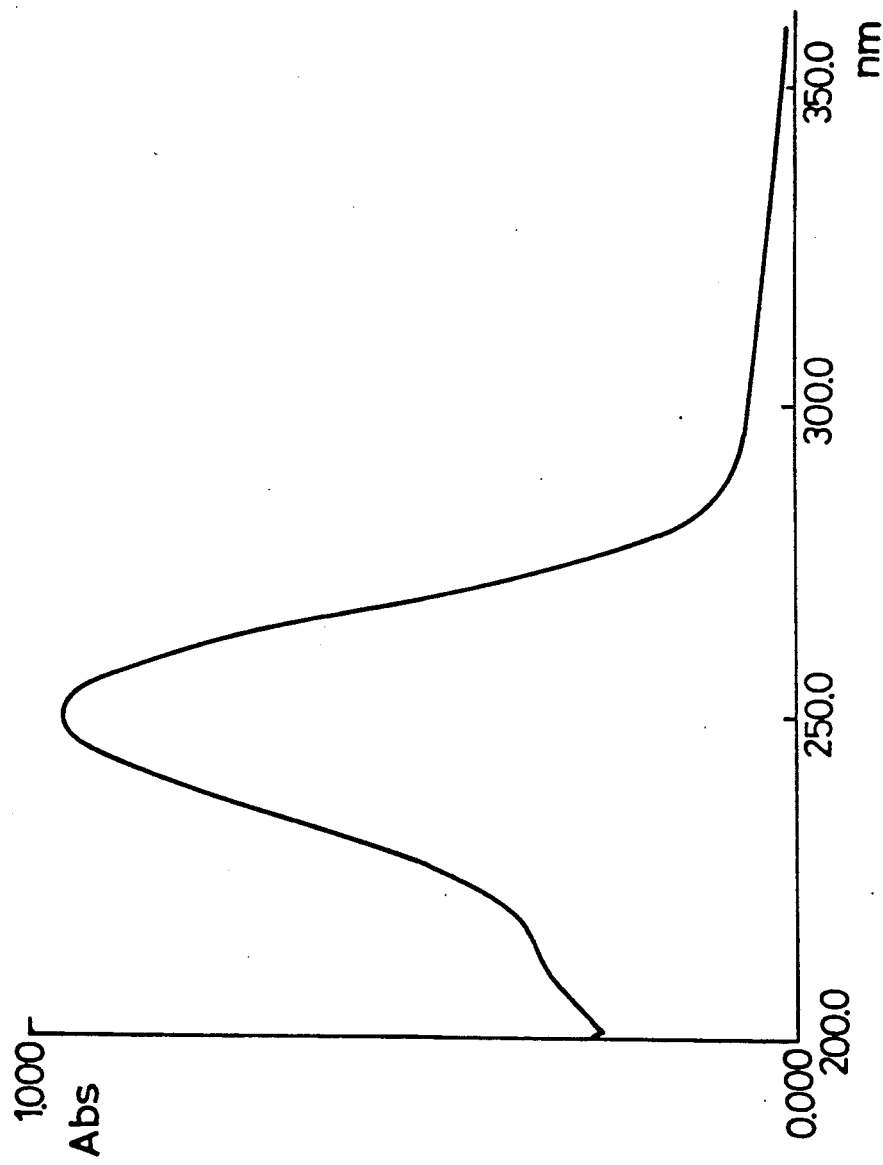
FIG. 1 shows the UV absorption spectrum.

An oxidation reaction facilitated in the process according to the present invention is as follows:

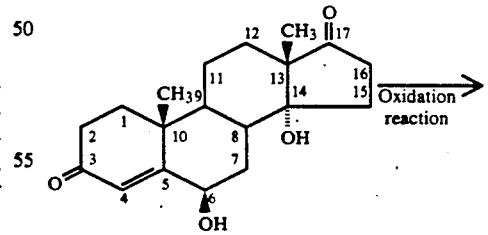

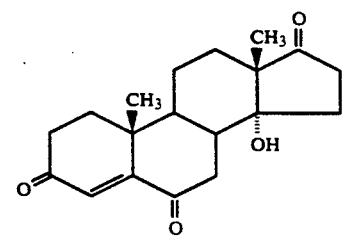

In order to selectively oxidize the 6β-hydroxyl group of a starting material of the formula shown above, according to the present invention, 6β,14α-dihydroxy-4-androstene-3,17-dione as the starting material is first dissolved in a halogenated hydrocarbon.

Said starting material may be obtained by the method disclosed in the above-mentioned U.S. Ser. No. 279,596, in which the above-mentioned starting material is produced by the action of *Acremonium strictum* on a known 4-androstene-3,17-dione as a substrate. In the process according to the present invention, independently of the production method or the degree of purity required, 6β,14α-dihydroxy-4-androstene-3,17-dione can be used as a starting material.

Examples of halogenated hydrocarbon solvents to dissolve said starting materials include chloroform, dichloromethane, dichloroethane, trichloroethane, ethyl bromide, dibromoethane, ethyl fluoride, propyl bromide and chlorobenzene; chloroform is preferably used.

In the above-mentioned solvent, 6β,14α-dihydroxy-4-androstene-3,17-dione is dissolved at a concentration of 5–200 g/liter, preferably 10–50 g/liter and placed in a reaction vessel. After blowing oxygen gas therein, said reaction vessel is sealed. Oxygen is blown directly into the solvent with a nozzle or the like or into the reaction vessel, so that the reaction vessel is sufficiently filled with oxygen gas. The reaction vessel is sealed immediately after so blowing oxygen gas.

As to the reaction vessel, a sealable glass vessel is preferably used; however, a plastic vessel which is solvent resistant may be used. Since the material forming the reaction vessel affects the transmissivity and transmissive wavelength of the light in the irradiation step to be followed, the selection thereof depends on the light source to be used.

Subsequently, the sealed reaction vessel is irradiated for 4 to 24 hours. Any light sources which emit light containing visible light can be used; for example, the sunlight, incandescent electric light, a white fluorescent lamp, a metal arc such as tungsten lamp, a carbon arc, a mercury arc and a discharge tube can be used. Namely, in order to selectively oxidize a starting material at position 6-β, wavelengths of visible rays (about 7800 to 3800 Å) are most effective as the source of the light energy. Generally, light sources with shorter wavelength having high chemical energy are not suitable, and light sources in which the ultraviolet area content is rather small and the portion of visible rays therein is 50% or more are preferably used. If the light energy is too high, the oxidation reaction on carbon atoms other than that at 6β position may occur, or the steroid structure itself may be affected, which interferes with the selective oxidation.

Since visible rays for the generation of the above-mentioned selective oxidation have to reach the solvent in which the starting substance is dissolved, the material from which the above-mentioned reaction vessel is formed is preferably selected so as not to interfere with transmission of the visible rays. For this, transparent glass is preferably used. Although the composition of the glass may affect the transmitted light, any kind of glass which does not interfere with the transmission of visible rays can be used.

Further, when a light source which emits light of many different wavelength areas as well as visible rays is used, an appropriate filter or an ultraviolet absorbing agent may be used so as to increase its ratio to visible rays.

The intensity of the light for the irradiation of the solvent is selected depending on the amount of the starting material to be treated and the material forming the reaction vessel. The intensity to be used ranges over 500 lux, which approximately corresponds to the range of the intensity of irradiation from a 40 W white fluorescent lamp at a distance of 10 cm to that of the sunlight. When the intensity of irradiation light is too strong, selective oxidation reaction as desired is difficult to achieve and when it is too weak, the oxidation reaction does not proceed. During the irradiation, temperature control is not particularly required unless the temperature of the solvent becomes excessively high. Room temperature is satisfactory for the reaction.

Then the solvent is removed, and 14α-hydroxy-4-androstene-3,6,17-trione can be recovered either by recrystallization from the resultant residue using organic solvents such as methanol, ethanol and acetone or by subjecting the residue to thin-layer chromatography or the like. According to the process of the present invention, it is possible to obtain the above-mentioned compound at a yield of 90% or more and even a yield of almost 100% can be achieved depending on the conditions.

The following Examples demonstrate the present invention more in detail.

In this regard, the method of identifying 14α-hydroxy-4-androstene-3,6,17-trione was disclosed in Japanese Patent Application No. 24594/1987 (integrated in U.S. Ser. No. 279,596) which had been previously applied by the present inventors. Namely, the compound of the present invention is specified to have the following physicochemical characteristics.

Figure 2:
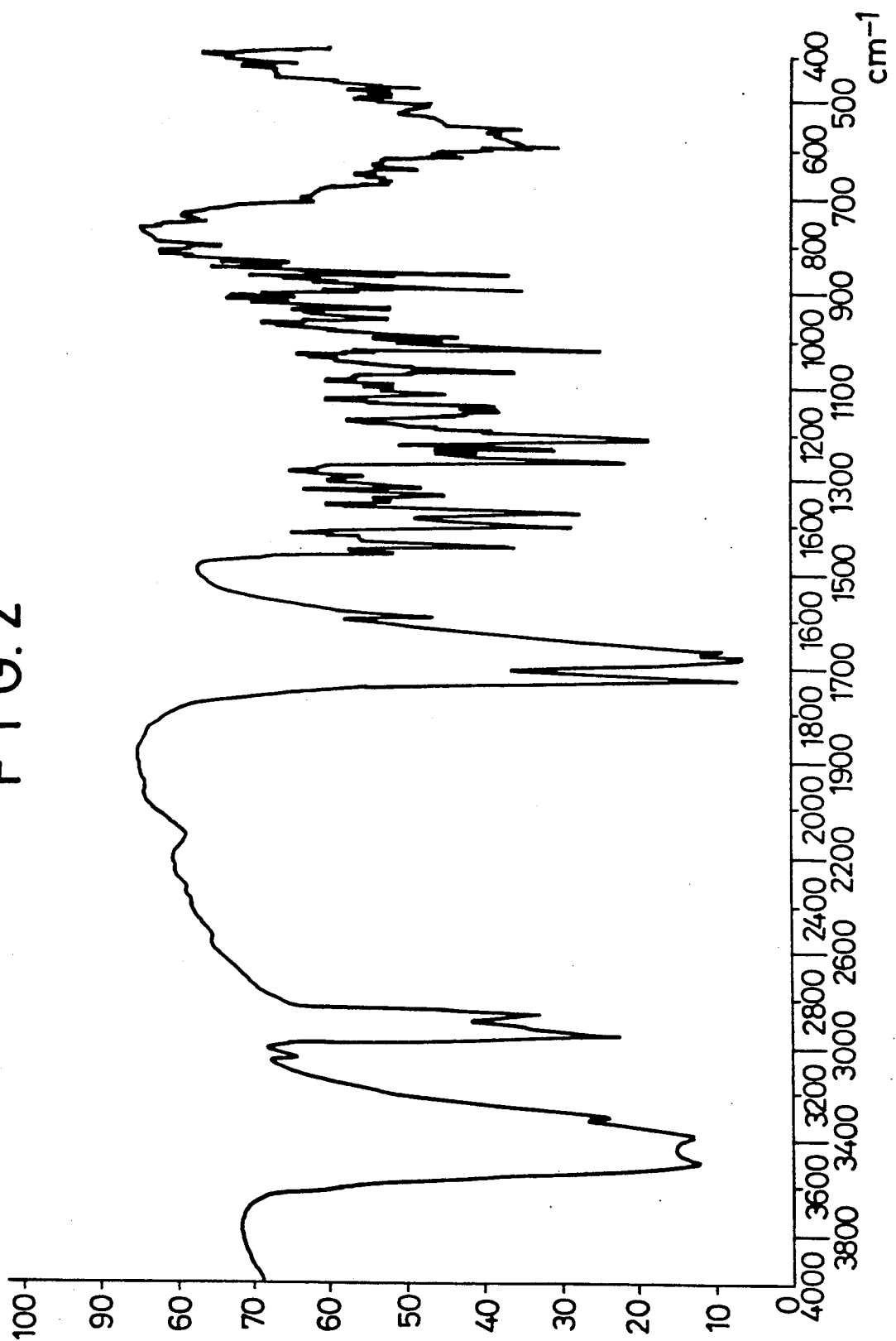
FIG. 2 shows the IR spectrum.
Figure 3:
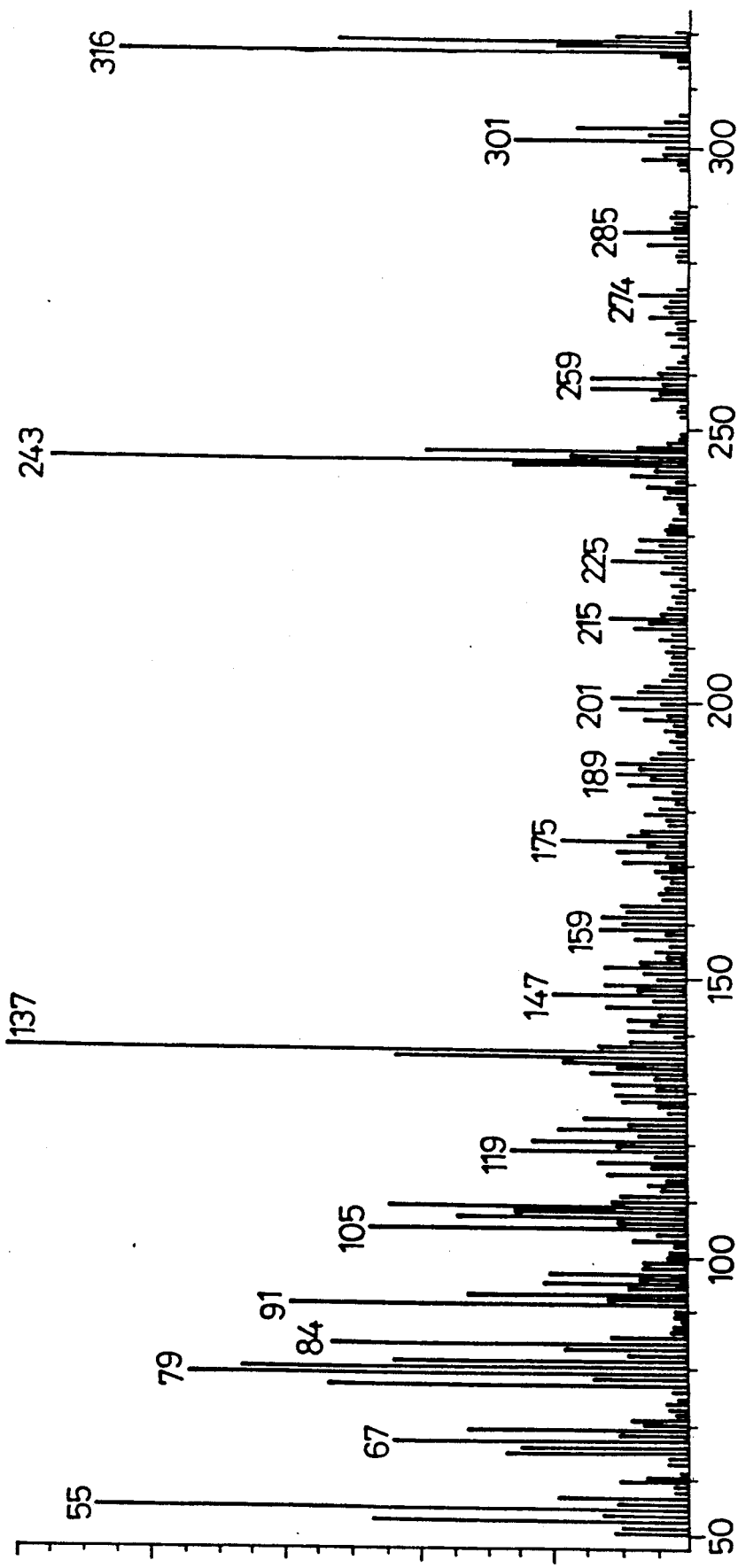
FIG. 3 shows the Mass spectrum.
Figure 4:
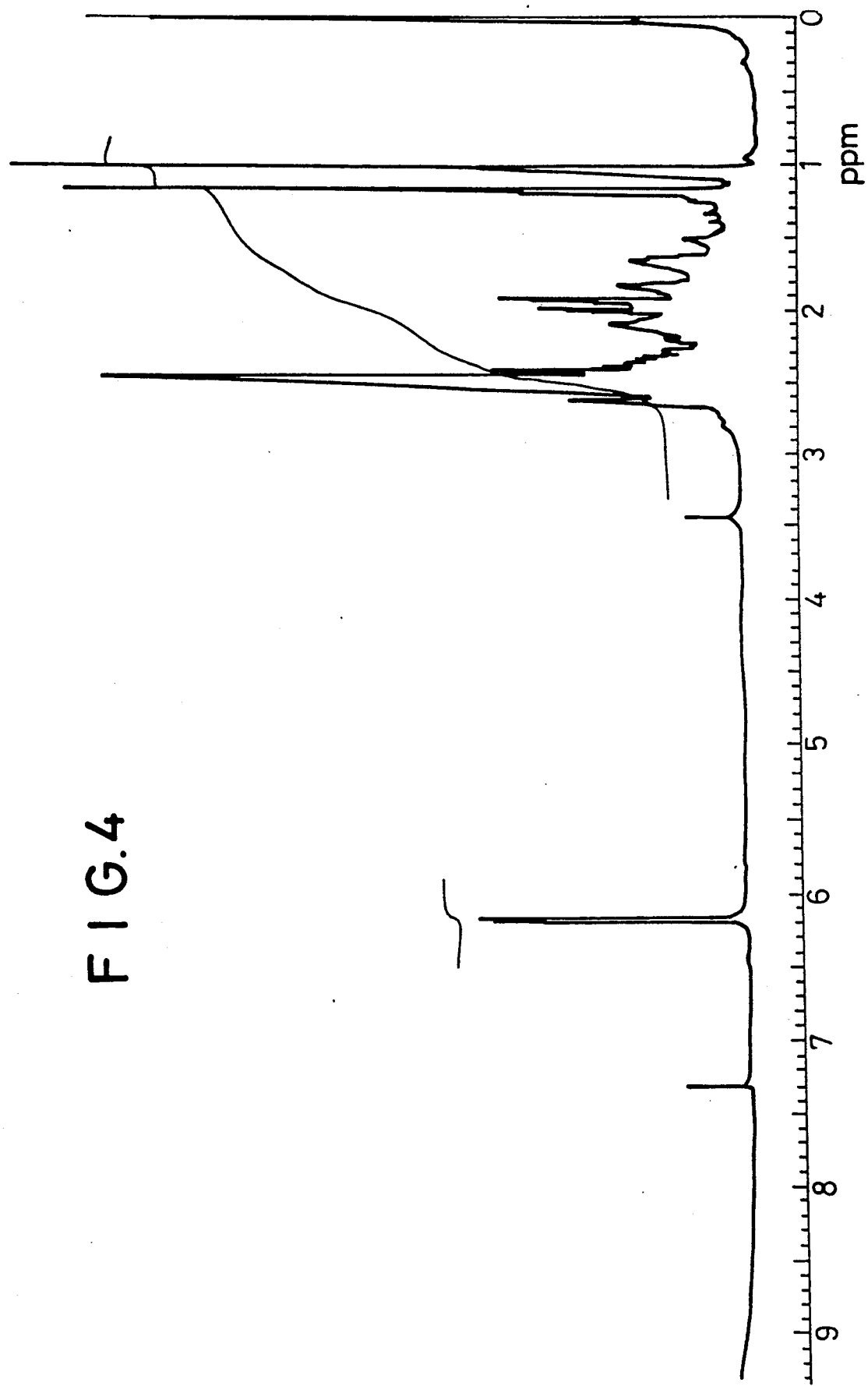
FIG. 4 shows the proton-NMR spectrum and
FIG. 5 shows the $^{13}$C-NMR spectrum.
Figure 5:
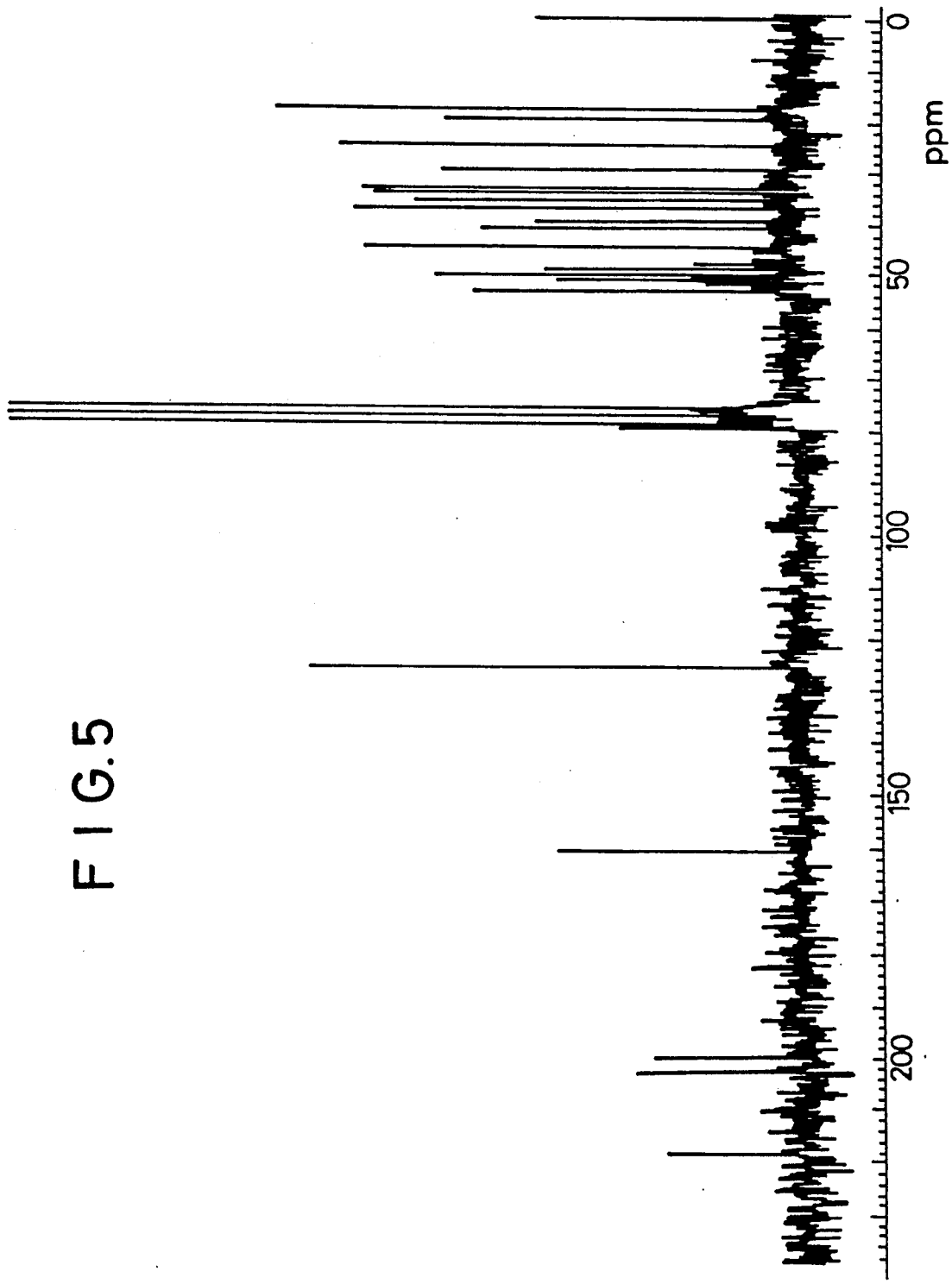

1) Appearance: White powder
2) Molecular weight: 316
3) Molecular formula: $C_{19}H_{24}O_4$
4) Ultraviolet absorption spectrum: See FIG. 1 attached
5) EI mass spectrum: m/Z=316, see FIG. 2
6) Infrared absorption spectrum (KBr method): 3520, 3410, 2790, 1735, 1690, 1675, 1605 $cm^{-1}$, see FIG. 3
7) Rf value (developing solvent, chloroform:methanol=9:1): 0.43
8) Solubility: Soluble in ethanol, methanol, ethyl acetate, and chloroform; insoluble in water and hexane
9) Melting point: 241°–244° C.

EXAMPLE 1

6β,14α-dihydroxy-4-androstene-3,17-dione used as a starting material in this Example was prepared according to the method disclosed in Japanese Patent Application No. 192798/1988 (also included in U.S. Ser. No. 279,596).

Namely, *Acremonium strictum* NN 106 (deposited at the Fermentation Research Institute, Agency of Industrial Science and Technology, Japan, under the deposition number of 9143) was cultured; after culturing, 4-androstene-3,17-dione was added to the culture as a substrate; steroid conversion was carried out by the microorganisms; solvent extraction from the culture was carried out; and finally purified preparation to be used was obtained.

6β,14α-dihydroxy-4-androstene-3,17-dione (50 g) thus prepared in the above-mentioned manner was dissolved in 1 liter of chloroform and transferred to a glass sealable vessel; after blowing oxygen therein, the vessel was sealed and allowed to stand for 4 hours under sunlight. Thereafter, the chloroform was removed by evaporation at 40° C. After the evaporation, the resultant residue was analyzed by thin layer chromatography and a spot for 14α-hydroxy-4-androstene-3,6,17-trione only was confirmed. According to this method, 49.2 g of 14α-hydroxy-4-androstene-3,6,17-trione was obtained. The yield was 98.4%.

EXAMPLE 2

6β,14α-dihydroxy-4-androstene-3,17-dione (1 gram) obtained in the same manner as described in Example 1 was dissolved in 100 ml of chloroform and transferred to a 300 ml glass flask with a screw cap. After blowing oxygen therein, the flask was sealed and then irradiated with the light of a white fluorescent lamp (50 W) at a distance of 10 cm for 12 hours at room temperature. Thereafter, chloroform was evaporated at 40° C. under reduced pressure. The resultant residue was dissolved in methanol and then cooled for recrystallization. Thus, 0.9 g of crystallized 14α-hydroxy-4-androstene-3,6,17-trione was obtained.

The UV absorption spectrum, IR absorption spectrum, mass spectrum and proton NMR and $^{13}$C-NMR measurements for the crystallized compound revealed that the 14α-hydroxy-4-androstene-3,6,17-trione thus obtained was identical to that previously reported. These absorption spectra are shown in FIGS. 1 to 5.

EXAMPLE 3

6β,14α-dihydroxy-4-androstene-3,17-dione (1 gram) obtained in the same manner as described in Example 1 was dissolved in 100 ml of chloroform and transferred to a 300-ml glass flask with a screw cap. After blowing oxygen therein, the flask was sealed and then irradiated with the light of a tungsten lamp (80 W) at a distance of 10 cm for 12 hours at room temperature. Thereafter, the chloroform was evaporated at 40° C. under reduced pressure. The resultant residue was dissolved in methanol and then cooled for recrystallization. Thus, 0.95 gram of 14α-hydroxy-4-androstene-3,6,17-trione was obtained.

The UV absorption spectrum, IR absorption spectrum, Mass spectrum and proton NMR and $^{13}$C-NMR analyses for the crystallized compound revealed that the 14α-hydroxy-4-androstene-3,6,17-trione thus obtained was identical to that previously reported. These absorption spectra are shown in FIGS. 1 to 5.

Although the invention has been described with reference to preferred embodiments, it is to be understood that variations and modifications will be apparent to those skilled in the art and are included within the invention. Such variations and modifications are to be considered within the purview and the scope of the claims appended hereto.

What is claimed is:

1. A process for the preparation of 14α-hydroxy-4-androstene-3,6,17-trione, comprising the steps of dissolving 6β,14α-dihydroxy-4-androstene-3,17-dione in a halogenated hydrocarbon solvent; sealing the reaction system after blowing oxygen therein; irradiating the system with light containing visible rays to selectively oxidize the hydroxyl group at position 6β; and recovering the thus-produced 14α-hydroxy-4-androstene-3,6,17-dione.

2. A process as set forth in claim 1, in which said halogenated hydrocarbon solvent is chloroform.

3. A process as set forth in claim 2, in which a light source is employed whose visible ray portion is at least 50% of the total irradiation spectrum thereof.

4. A process as set forth in claim 2, in which the irradiation is carried out at a light intensity of from 500 lux to sunlight intensity.

5. A process as set forth in claim 3, wherein the halogenated hydrocarbon solvent is chloroform.

6. A process as set forth in claim 4, wherein the halogenated hydrocarbon solvent is chloroform.

* * * * *